(12) United States Patent
Lee et al.

(10) Patent No.: US 8,281,642 B2
(45) Date of Patent: Oct. 9, 2012

(54) ENVIRONMENTAL GAS SENSOR AND METHOD OF MANUFACTURING THE SAME

(75) Inventors: Su Jae Lee, Daejeon (KR); Jin Ah Park, Daejeon (KR); Jae Hyun Moon, Daejeon (KR); Seong Hyun Kim, Daejeon (KR); Tae Hyoung Zyung, Daejeon (KR); Hye Yong Chu, Daejeon (KR)

(73) Assignee: Electronics and Telecommunications Research Institute, Daejeon (KR)

( * ) Notice: Subject to any disclaimer, the term of this patent is extended or adjusted under 35 U.S.C. 154(b) by 345 days.

(21) Appl. No.: 12/787,806

(22) Filed: May 26, 2010

(65) Prior Publication Data

US 2011/0120866 A1     May 26, 2011

(30) Foreign Application Priority Data

Nov. 23, 2009  (KR) .................. 10-2009-0113128

(51) Int. Cl.
    *G01N 27/04* (2006.01)
(52) U.S. Cl. ...... 73/31.01; 73/23.2; 73/23.31; 73/23.32; 73/23.34; 73/31.03
(58) Field of Classification Search ............ 73/23.2, 73/23.3, 23.31, 23.32, 23.34, 31.01, 31.02, 73/31.05, 31.06
    See application file for complete search history.

(56) References Cited

U.S. PATENT DOCUMENTS

| | | | |
|---|---|---|---|
| 6,905,655 B2 * | 6/2005 | Gabriel et al. ............. | 422/82.01 |
| 7,186,381 B2 * | 3/2007 | Penner et al. .................. | 422/98 |
| 7,528,695 B2 | 5/2009 | Conley, Jr. et al. | |
| 7,640,789 B2 | 1/2010 | Kim et al. | |
| 7,762,121 B2 * | 7/2010 | Ng et al. ..................... | 73/23.31 |
| 8,087,151 B2 * | 1/2012 | Park et al. .................... | 29/592.1 |
| 2002/0117659 A1 * | 8/2002 | Lieber et al. .................... | 257/14 |
| 2003/0118815 A1 * | 6/2003 | Rodriguez et al. ............ | 428/368 |
| 2004/0173506 A1 * | 9/2004 | Doktycz et al. ................. | 210/85 |
| 2004/0238367 A1 * | 12/2004 | Penner et al. .................. | 205/76 |
| 2005/0007002 A1 * | 1/2005 | Golovchenko et al. ....... | 313/311 |
| 2005/0072213 A1 * | 4/2005 | Besnard et al. ............. | 73/31.06 |
| 2005/0126909 A1 | 6/2005 | Weiller et al. | |
| 2005/0155858 A1 * | 7/2005 | Monty et al. .................. | 204/424 |
| 2006/0185980 A1 | 8/2006 | Fukuda | |
| 2006/0284218 A1 | 12/2006 | Kaner et al. | |

(Continued)

FOREIGN PATENT DOCUMENTS

JP     2006-226860     8/2006

(Continued)

OTHER PUBLICATIONS

Yang Zhang et al., "Fabrication and ethanol-sensing properties of micro gas sensor based on electrospun $SnO_2$ nanofibers", ScienceDirect, Sensors and Actuators B 132 (2008) 67-73.

(Continued)

*Primary Examiner* — David Rogers
(74) *Attorney, Agent, or Firm* — Rabin & Berdo, P.C.

(57) ABSTRACT

Provided are an environmental gas sensor and a method of manufacturing the same. The environmental gas sensor includes an insulating substrate, metal electrodes formed on the insulating substrate, and a sensing layer in which different kinds of nanofibers are arranged perpendicular to each other on the metal electrodes. Thus, the environmental gas sensor can simultaneously sense two kinds of gases.

15 Claims, 3 Drawing Sheets

U.S. PATENT DOCUMENTS

| | | | |
|---|---|---|---|
| 2007/0114138 A1 | 5/2007 | Krasteva et al. | |
| 2007/0117213 A1* | 5/2007 | Cole et al. | 436/146 |
| 2007/0261959 A1 | 11/2007 | Kim et al. | |
| 2008/0150556 A1 | 6/2008 | Han et al. | |
| 2010/0007625 A1* | 1/2010 | Jiang et al. | 345/173 |
| 2010/0239488 A1* | 9/2010 | Zettl et al. | 423/447.1 |
| 2010/0245808 A1* | 9/2010 | Xiao et al. | 356/218 |
| 2011/0147715 A1* | 6/2011 | Rogers et al. | 257/24 |

FOREIGN PATENT DOCUMENTS

| | | |
|---|---|---|
| JP | 2007-171207 | 7/2007 |
| JP | 2007-187476 A | 7/2007 |
| JP | 2007-225596 | 9/2007 |
| JP | 2008-83041 | 4/2008 |
| KR | 2007-0066859 A | 6/2007 |
| KR | 2009-0060837 A | 6/2009 |
| KR | 2009-0101906 A | 9/2009 |
| WO | WO 2008/079703 A1 | 7/2008 |

OTHER PUBLICATIONS

Isabelle Raible et al., "$V_2O_5$ nanofibres: novel gas sensors with extremely high sensitivity and selectivity to amines", ScienceDirect, Sensors and Actuators B 106 (2005) 730-735.

Tzong-Rong Ling et al., "Influence of nano-scale dopants of Pt, CaO and $SiO_2$, on the alcohol sensing of $SnO_2$ thin films", ScienceDirect, Sensors and Actuators B 119 (2006) 497-503.

* cited by examiner

ENVIRONMENTAL GAS SENSOR AND METHOD OF MANUFACTURING THE SAME

CROSS-REFERENCE TO RELATED APPLICATION

This application claims priority to and the benefit of Korean Patent Application No. 10-2009-0113128, filed Nov. 23, 2009, the disclosure of which is incorporated herein by reference in its entirety.

BACKGROUND

1. Field of the Invention

The present invention relates to an environmental gas sensor and a method of manufacturing the same, and more particularly, to an environmental gas sensor which can simultaneously measure two kinds of gases through a sensing layer on which different kinds of nanofibers are arranged perpendicular to each other.

2. Discussion of Related Art

In recent times, growing concerns about environmental pollution and health have increased the necessity to sense various environmentally-harmful gases. The demand for a harmful gas sensor which has developed in response to the demand to sense toxic and explosive gases is growing to increase the quality of human life through, for example, health care, monitoring of living environment, industrial health and safety, home appliances and home automation, food and agriculture, manufacturing processes, and national defense and terror.

Thus, the gas sensor will become a means for building a disaster-free future society, and must adapt to more precisely measure and control environmentally-harmful gases.

Since new services such as a ubiquitous sensor system and an environmental sensing system are being realized, such a sensor system should satisfy several conditions in order to be commercialized. First, the gas sensor should have high sensitivity so that it can detect a low-concentration gas. Second, the gas sensor should have selectivity so that it can selectively sense a specific gas without influencing a co-existing gas. Third, the gas sensor should have stability, so that it does not influence surrounding ambient temperature and humidity and stably senses a gas, and should not be degraded according to time. Fourth, the gas sensor should have fast response speed, so that it can rapidly and repeatedly react with gases. Fifth, the gas sensor should have multi-functionality and low power consumption. To meet these conditions, there are various attempts to develop a novel material for a sensor and a gas sensor.

Examples of gas sensors using ceramic include a semiconductor gas sensor, a solid electrolyte gas sensor, and a catalytic combustible gas sensor, which are distinguished by type, structure and material. An environmental gas sensor having characteristic that when an oxide semiconductor ceramic such as zinc oxide (ZnO), tin oxide ($SnO_2$), tungsten oxide ($WO_3$), titanium oxide ($TiO_2$), or indium oxide ($In_2O_3$) is in contact with an environmental gas such as $H_2$, CO, $O_2$, $CO_2$, $NO_x$, a toxic gas, a volatile organic gas, ammonia, or moisture, electrical resistivity is changed due to gas adsorption and oxidation/reduction, which occur at a surface of a metal oxide, has been widely researched. Such an environmental gas sensor is used as a commercially-available gas sensor.

Recently, much research on developing a gas sensor using an oxide semiconductor having a nano structure such as a nano thin film, nanoparticle, nanowire, nanofiber, nanotube, nanopore, or nanobelt, which has different characteristics from a bulk material has been progressing. A small size, particularly, a high surface-to-volume ratio, of this nano structure material enables manufacture of a sensor having fast response speed and high sensitivity. Such a novel material enables development of a gas sensor having excellent characteristics such as fast response speed, high sensitivity, high selectivity, and low power consumption.

However, a gas sensor using an oxide having a nano structure such as zinc oxide (ZnO), tin oxide ($SnO_2$), tungsten oxide ($WO_3$), titanium oxide ($TiO_2$), or indium oxide ($In_2O_3$) is designed to sense a single gas, and thus cannot detect various environmental gases at the same time. To detect various environmental gases, a sensor formed in an array structure is needed.

Thus, a new approach to novel sensor materials, structures and processes is needed to develop a gas sensor compensating disadvantages of the conventional gas sensor formed of an oxide semiconductor and having excellent characteristics such as high sensitivity, high selectivity, fast response speed and long-term stability. To this end, today, the development of an oxide semiconductor nanofiber and a method of preparing the same, and a gas sensor using the same is actively progressing.

As a result, the present inventors found that by using a sensing layer in which different kinds of nanofibers are arranged, two kinds of gases can be sensed at the same time during development of an environmental gas sensor having high sensitivity, fast response, high selectivity, and long-term stability using a characteristic high specific surface area of a nanofiber, and thus completed the present invention.

SUMMARY OF THE INVENTION

The present invention is directed to an environmental gas sensor which can simultaneously sense two kinds of gases.

The present invention is also directed to a method of manufacturing an environmental gas sensor which can simultaneously sense two kinds of gases.

One aspect of the present invention provides an environmental gas sensor, including: an insulating substrate; metal electrodes formed on the insulating substrate; and a sensing layer in which different kinds of nanofibers are arranged perpendicular to each other on the metal electrodes.

In the environmental gas sensor according to the present invention, the insulating substrate may be selected from the group consisting of a single crystalline oxide substrate, a ceramic substrate, a silicon semiconductor substrate, a glass substrate, an insulating substrate including a microheater a bottom or top thereof, and a micromachine structure substrate including a microheater therein, and have a thickness of 0.1 to 1 mm.

In the environmental gas sensor according to the present invention, the metal electrodes may include at least one selected from the group consisting of platinum (Pt), palladium (Pd), gold (Au), silver (Ag), aluminum (Al), nickel (Ni), titanium (Ti), copper (Cu), chromium (Cr), tin (Sn), molybdenum (Mo), ruthenium (Ru) and indium (In), and have a thickness of 10 to 1000 nm.

In the environmental gas sensor according to the present invention, one of the different kinds of nanofibers may be an n-type oxide semiconductor compound, and the other one of the nanofibers may be a p-type oxide semiconductor compound. The n-type oxide semiconductor compound may include at least one selected from the group consisting of an $ABO_3$-type perovskite oxide ($BaTiO_3$, metal-doped $BaTiO_3$, $SrTiO_3$, or $BaSnO_3$), MgO, CaO, $TiO_2$, $ZrO_2$, $V_2O_5$, $Nb_2O_5$, $Ta_2O_5$, $MoO_3$, $WO_3$, ZnO, $Al_2O_3$, $Ga_2O_3$, $In_2O_3$, and $SnO_2$, and the p-type oxide semiconductor compound may include at least one selected from the group consisting of $Y_2O_3$, $La_2O_3$, $CeO_3$, $Mn_2O_3$, $CO_2O_4$, NiO, PdO, $Ag_2O$, $Bi_2O_3$, $Sb_2O_3$, CuO, and $TeO_2$.

In the environmental gas sensor according to the present invention, the metal electrodes may include a pair of first metal electrodes between which one of the different kinds of nanofibers is arranged, and a pair of second metal electrodes between which the other one of the nanofibers is arranged. The nanofiber arranged may have a diameter of 1 to 1000 nm.

Another aspect of the present invention provides a method of manufacturing an environmental gas sensor, including: forming metal electrodes on an insulating substrate; arranging different kinds of nanofibers perpendicular to each other on the metal electrodes through electrospinning; and forming a sensing layer by heat-treating the different kinds of nanofibers arranged.

According to the method of manufacturing an environmental gas sensor of the present invention, the process of arranging different kinds of nanofibers perpendicular to each other may include: arranging one of the different kinds of nanofibers by electrospinning a combination solution containing a first semiconductor and a first polymer on a pair of first metal electrodes; and arranging the other one of the nanofibers perpendicular to the previously-arranged nanofiber by electrospinning a combination solution containing a second oxide semiconductor and a second polymer on a pair of second metal electrodes. Here, the first oxide semiconductor may be an n-type semiconductor oxide, and the second oxide semiconductor may be a p-type semiconductor oxide, or the first oxide semiconductor may be a p-type semiconductor oxide, and the second oxide semiconductor may be an n-type semiconductor oxide.

According to the method of manufacturing an environmental gas sensor of the present invention, the combination solution containing first or second oxide semiconductor and polymer may be prepared by mixing an oxide precursor, a polymer and a solvent, and stirring the resulting mixture at room temperature or more.

BRIEF DESCRIPTION OF THE DRAWINGS

The above and other features and advantages of the present invention will become more apparent to those of ordinary skill in the art by describing in detail preferred embodiments thereof with reference to the attached drawings in which.

DETAILED DESCRIPTION OF EXEMPLARY EMBODIMENTS

Hereinafter, exemplary embodiments of the present invention will be described in detail. However, the present invention is not limited to the embodiments disclosed below, but can be implemented in various forms. Therefore, the following embodiments are described in order for this disclosure to be complete and enabling to those of ordinary skill in the art.

Figure 1:
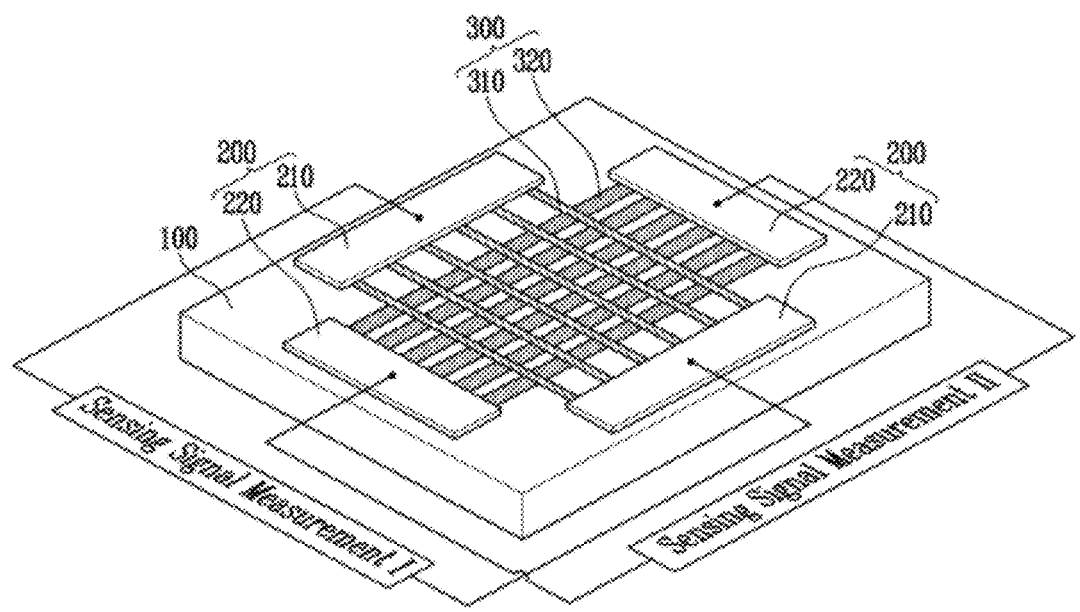
FIG. 1 is a perspective view of an environmental gas sensor in which different kinds of nanofibers are arranged perpendicular to each other according to the present invention.

FIG. 1 is a perspective view of an environmental gas sensor according to the present invention.

Referring to FIG. 1, an environmental gas sensor according to the present invention includes an insulating substrate 100, metal electrodes 200 formed on the insulating substrate 100, and a sensing layer 300 in which different kinds of nanofibers are arranged perpendicular to each other on the metal electrodes 200.

The insulating substrate 100 may be selected from the group consisting of a single-crystalline oxide ($Al_2O_3$, MgO, or $SrTiO_3$) substrate, a ceramic substrate ($Al_2O_3$ or quartz), a silicon semiconductor substrate ($SiO_2$/Si), and a glass substrate, each having a thickness of 0.1 to 1 mm.

The insulating substrate 100 may be designed to have a microheater on a bottom or top thereof, or a micromachine structure including a microheater therein.

The metal electrode 200 may be formed of one selected from the group consisting of Pt, Pd, Ag, Au, Ni, Ti, Cr, Al, Cu, Sn, Mo, Ru and In to have a thickness of 10 to 1000 nm.

The metal electrode 200 may include two pairs of metal electrodes 210 and 220, between which different kinds of nanofibers are arranged. Here, the metal electrodes 210 and 220 may be formed of the same or different materials, and each pair of metal electrodes 210 or 220 may be disposed to face each other on the tetragonal insulating substrate.

Different kinds of nanofibers I 310 and II 320 are arranged perpendicular to each other on or between the metal electrodes 200. The nanofibers I 310 or II 320 may be selected from organic and inorganic semiconductor nanofibers, and have high responsiveness to a different gas. Preferably, the nanofiber I 310 and the nanofiber II 320 arranged perpendicular to the nanofiber I 310 are formed of different materials from each other, and more preferably, semiconductors having different semi-conductivities (n-type and p-type semiconductors) from each other.

Either of the nanofibers I 310 and II 320 arranged may include an oxide semiconductor selected from the group consisting of n-type semiconductors such as an $ABO_3$-type perovskite oxide ($BaTiO_3$, metal-doped $BaTiO_3$, $SrTiO_3$, or $BaSnO_3$), MgO, CaO, $TiO_2$, $ZrO_2$, $V_2O_5$, $Nb_2O_5$, $Ta_2O_5$, $MoO_3$, $WO_3$, ZnO, $Al_2O_3$, $Ga_2O_3$, $In_2O_3$, and $SnO_2$, and/or the group consisting of p-type semiconductors such as $Y_2O_3$, $La_2O_3$, $CeO_3$, $Mn_2O_3$, $CO_2O_4$, NiO, PdO, $Ag_2O$, $Bi_2O_3$, $Sb_2O_3$, CuO, and $TeO_2$.

The nanofiber may have a diameter of 1 to 1000 nm to increase a specific area and thus increase responsiveness to a specific gas.

Figure 2:
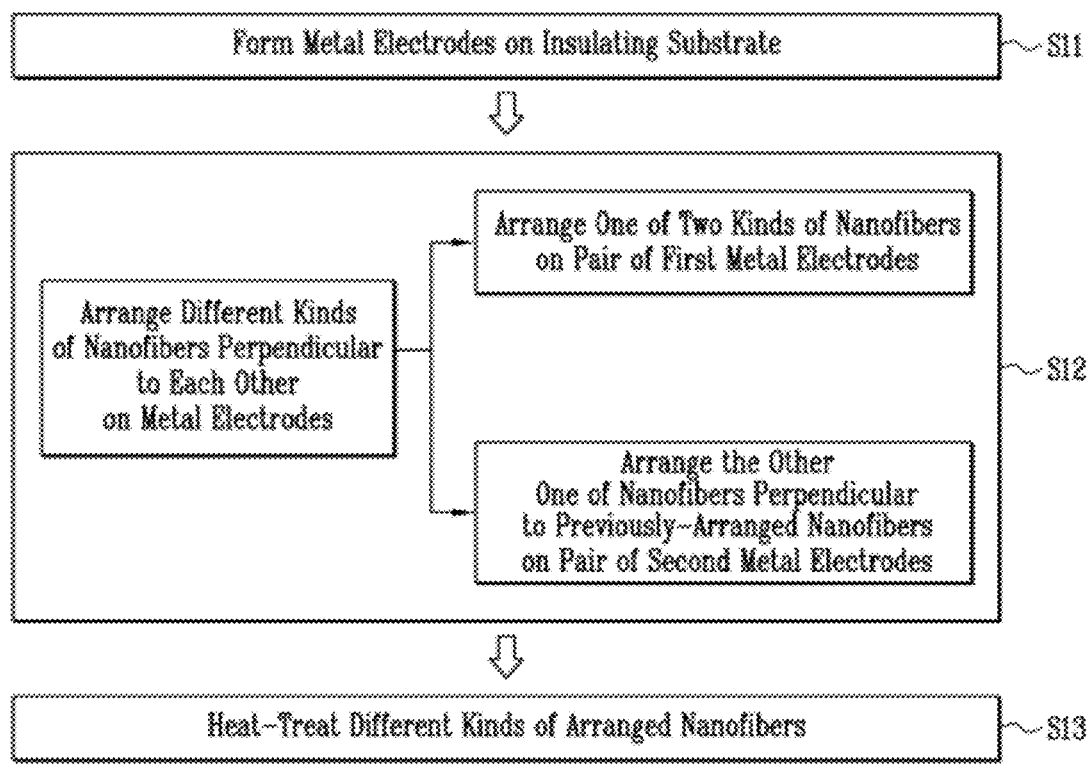
FIG. 2 is a flow chart illustrating a manufacturing process of an environmental gas sensor in which different kinds of nanofibers are arranged perpendicular to each other according to the present invention.

FIG. 2 is a flow chart illustrating a method of manufacturing an environmental gas sensor according to the present invention.

Referring to FIG. 2, a method of manufacturing an environmental gas sensor according to the present invention includes: forming metal electrodes on an insulating substrate (S11); arranging different kinds of nanofibers perpendicular to each other on the metal electrodes through electrospinning (S12); and forming a sensing layer by performing heat treatment on the different kinds of nanofibers arranged (S13).

To manufacture the oxide nanofiber gas sensor, to begin with, metal electrodes are formed on an insulating substrate (S11). Here, the metal electrode may be formed of one selected from the group consisting of Pt, Pd, Ag, Au, Ni, Ti, Cr, Al, Cu, Sn, Mo, Ru and In. The metal electrode may be formed to a thickness of 10 to 1000 nm by a common method in the art. According to the present invention, there are two pairs of metal electrodes on the insulating substrate, and each pair of metal electrodes may be disposed so as to face each other.

Subsequently, different kinds of nanofibers are arranged perpendicular to each other between the metal electrodes through electro spinning (S12).

The process of arranging the different kinds of nanofibers perpendicular to each other on the metal electrodes may include: arranging one of the different kinds of nanofiber by electrospinning a combination solution containing a first oxide semiconductor and a first polymer on a pair of first metal electrodes; and arranging the other one of the different kinds of nanofiber perpendicular to the previously-arranged nanofiber by electrospinning a different combination solution containing a second oxide semiconductor and a second polymer on a pair of second metal electrodes.

Here, the combination solution may be prepared by mixing a metal oxide or metal oxide precursor, a polymer and a solvent, and may have a viscosity of 1000 to 3000 cps to be suitable for electrospinning. The polymer and the solvent may be a combination of a polar polymer-polar solvent, or a nonpolar polymer-nonpolar solvent. The combination solution is mixed at room temperature or more (e.g., 25 to 100° C.), and should be stirred for a long time (specifically for 3 to 24 hours) to prepare a bead-free nanofiber.

As the metal oxide used to prepare the combination solution, at least one selected from the group consisting of n-type semiconductors such as an $ABO_3$-type perovskite oxide ($BaTiO_3$, metal-doped $BaTiO_3$, $SrTiO_3$, or $BaSnO_3$), MgO, CaO, $TiO_2$, $ZrO_2$, $V_2O_5$, $Nb_2O_5$, $Ta_2O_5$, $MoO_3$, $WO_3$, ZnO, $Al_2O_3$, $Ga_2O_3$, $In_2O_3$, and $SnO_2$, or at least one selected from the group consisting of p-type semiconductors such as $Y_2O_3$, $La_2O_3$, $CeO_3$, $Mn_2O_3$, $CO_2O_4$, NiO, PdO, $Ag_2O$, $Bi_2O_3$, $Sb_2O_3$, CuO, and $TeO_2$ may be used.

As the polymer, polyvinylphenol (PVP), polyvinylalcohol (PVA), polyvinylacetate (PVAc), polystyrene (PS), polyethylene oxide (PEO), polyether urethane (PU), polycarbonate (PC), poly-L-lactate (PLLA), polyvinylcarbazole, polyvinyl chloride (PVC), polycaprolactam, polyethylene terephthalate (PET), or polyethylene naphthalate (PEN) may be used, and as the solvent, ethanol, acetone, dimethylformamide (DMF), tetrahydrofuran (THF), isopropyl alcohol (IPA), water, chloroform, formic acid, dimethylformamide (DEF), dimethylacetamide (DMA), dichloromethane, toluene, or acetic acid may be used.

The combination solution is contained in a cylinder of an electrospinning device to be spun through an injection nozzle. Here, a voltage of 1 to 30 kV is applied to the injection nozzle, and thus the combination solution is spun and collected on a substrate on a ground collector, thereby obtaining a nanofiber having a diameter of 1 to 1000 nm.

Subsequently, heat treatment is performed on the different nanofibers arranged, thereby forming a sensing layer (S13). Here, the heat treatment is performed to remove the solvent and induce crystallization, and may be performed at a high temperature of 100 to 1000° C.

Hereinafter, the present invention will be described in further detail with reference to Example, but is not limited thereto.

EXAMPLE

Figure 3:
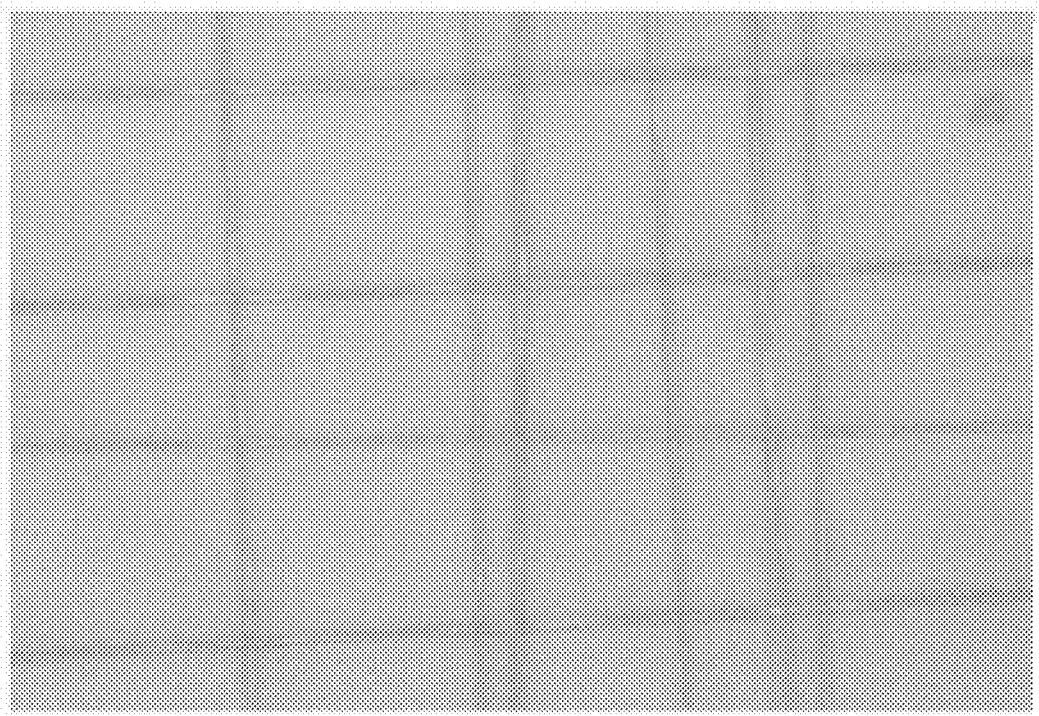
FIG. 3 is an optical microscopic photograph of a surface of different kinds of nanofibers designed to be arranged perpendicular to each other according to an exemplary embodiment of the present invention.

A pair of metal electrodes (Pt) facing each other were formed to a thickness of 100 nm, and another pair of metal electrodes (Pt) facing each other were formed to a thickness of 100 nm, on a quartz substrate having a thickness of 0.5 mm. Subsequently, a metal oxide (ZnO) precursor, poly(4-vinyl phenol) (PVP), and ethanol were mixed in a weight ratio of 5:3:1, and stirred at 60° C. for 24 hours, thereby preparing a ZnO/PVP combination solution having a viscosity of 1200 cps. Afterwards, the ZnO/PVP combination solution was spun using an electrospinning device to arrange one kind of nanofiber on a pair of metal electrodes. In addition, a metal oxide (NiO) precursor, PVP, and ethanol were mixed in a weight ratio of 5:3:1, and stirred at 60° C. for 24 hours, thereby preparing a NiO/PVP combination solution having a viscosity of 1200 cps. Subsequently, the NiO/PVP combination solution was spun by an electrospinning device, thereby arranging a different kind of nanofiber to be disposed perpendicular to the previously arranged nanofiber on the pair of metal electrodes on another pair of metal electrodes. A photograph of a surface on which different kinds of nanofibers were arranged perpendicular to each other to manufacture the environmental gas sensor was taken using an optical microscope. The result is shown in FIG. 3. Referring to FIG. 3, it can be confirmed that different kinds of nanofibers are arranged perpendicular to each other.

The present invention provides an environmental gas sensor including a sensing layer having a structure in which one kind of nanofiber having responsiveness to a specific gas is arranged perpendicular to a different kind of nanofiber having responsiveness to an another gas. The gas sensor can simultaneously sense two kinds of gases, and thus can be applied to next-generation ubiquitous sensor systems, and environmental sensor systems, which need to more precisely measure and control various environmentally-harmful gases.

While the invention has been shown and described with reference to certain exemplary embodiments thereof, it will be understood by those skilled in the art that various changes in form and details may be made therein without departing from the spirit and scope of the invention as defined by the appended claims.

What is claimed is:

1. An environmental gas sensor, comprising:
    an insulating substrate;
    metal electrodes formed on the insulating substrate; and
    a sensing layer in which different kinds of nanofibers are arranged perpendicular to and overlapping each other on the metal electrodes.

2. The sensor of claim 1, wherein the insulating substrate is selected from the group consisting of a single crystalline oxide substrate, a ceramic substrate, a silicon semiconductor substrate, a glass substrate, an insulating substrate including a microheater on a bottom or top thereof, and a micromachine structure substrate including a microheater therein.

3. The sensor of claim 1, wherein the insulating substrate has a thickness of 0.1 to 1 mm.

4. The sensor of claim 1, wherein each of the metal electrodes includes at least one selected from the group consisting of platinum (Pt), palladium (Pd), gold (Au), silver (Ag), aluminum (Al), nickel (Ni), titanium (Ti), copper (Cu), chromium (Cr), tin (Sn), molybdenum (Mo), ruthenium (Ru) and indium (In).

5. The sensor of claim 1, wherein each of the metal electrodes has a thickness of 10 to 1000 nm.

6. The sensor of claim 1, wherein the different kinds of nanofibers are selected from organic and inorganic semiconductor nanofibers having high responsiveness to different specific gases.

7. The sensor of claim 6, wherein one of the different kinds of nanofibers is an n-type oxide semiconductor compound, and the other one of the nanofibers is a p-type oxide semiconductor compound.

8. The sensor of claim 7, wherein the n-type oxide semiconductor compound includes at least one selected from the group consisting of an $ABO_3$-type perovskite oxide ($BaTiO_3$, metal-doped $BaTiO_3$, $SrTiO_3$, or $BaSnO_3$), MgO, CaO, $TiO_2$, $ZrO_2$, $V_2O_5$, $Nb_2O_5$, $Ta_2O_5$, $MoO_3$, $WO_3$, $ZnO$, $Al_2O_3$, $Ga_2O_3$, $In_2O_3$, and $SnO_2$, and the p-type oxide semiconductor compound includes at least one selected from the group consisting of $Y_2O_3$, $La_2O_3$, $CeO_3$, $Mn_2O_3$, $CO_2O_4$, $NiO$, $PdO$, $Ag_2O$, $Bi_2O_3$, $Sb_2O_3$, $CuO$, and $TeO_2$.

9. The sensor of claim 1, wherein the metal electrodes include a pair of first metal electrodes between which one of the different kinds of nanofibers is arranged, and a pair of second metal electrodes between which the other one of the nanofibers is arranged.

10. The sensor of claim 1, wherein the nanofiber has a diameter of 1 to 1000 nm.

11. A method of manufacturing an environmental gas sensor, comprising:
   forming metal electrodes on an insulating substrate;
   arranging different kinds of nanofibers perpendicular to and overlapping each other on the metal electrodes through electrospinning; and
   forming a sensing layer by heat-treating the different kinds of nanofibers arranged.

12. The method of claim 11, wherein arranging the different kinds of nanofibers perpendicular to each other comprises:
   arranging one of the different kinds of nanofibers by electrospinning a combination solution having a first oxide semiconductor and a first polymer on a pair of first metal electrodes; and
   arranging the other one of the nanofibers perpendicular to the previously-arranged nanofiber by electrospinning a combination solution having a second oxide semiconductor and a second polymer on a pair of second metal electrodes.

13. The method of claim 12, wherein the first oxide semiconductor is an n-type semiconductor oxide, and the second oxide semiconductor is a p-type semiconductor oxide.

14. The method of claim 12, wherein the first oxide semiconductor is a p-type semiconductor oxide, and the second oxide semiconductor is an n-type semiconductor oxide.

15. The method of claim 12, wherein the combination solution including the first or second oxide semiconductor and polymer is prepared by mixing a metal oxide or metal oxide precursor, a polymer and a solvent, and stirring the resulting mixture at room temperature or more.

* * * * *